United States Patent
Sun et al.

(10) Patent No.: US 11,447,438 B2
(45) Date of Patent: Sep. 20, 2022

(54) PROCESS FOR PREPARING 3,3,3-TRIFLUOROPROP-1-ENE

(71) Applicant: THE CHEMOURS COMPANY FC, LLC, Wilmington, DE (US)

(72) Inventors: Xuehui Sun, Kennett Square, PA (US); Karl Robert Krause, Kennett Square, PA (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 17/246,783

(22) Filed: May 3, 2021

(65) Prior Publication Data

US 2021/0253503 A1 Aug. 19, 2021

Related U.S. Application Data

(62) Division of application No. 16/749,857, filed on Jan. 22, 2020, now Pat. No. 11,028,028, which is a division of application No. 15/917,376, filed on Mar. 9, 2018, now Pat. No. 10,577,296.

(60) Provisional application No. 62/469,668, filed on Mar. 10, 2017.

(51) Int. Cl.

| C07C 17/25 | (2006.01) |
|---|---|
| C07C 21/18 | (2006.01) |
| B01J 27/10 | (2006.01) |
| C07C 17/04 | (2006.01) |
| C07C 17/07 | (2006.01) |
| C07C 19/10 | (2006.01) |

(52) U.S. Cl.
CPC .............. *C07C 17/25* (2013.01); *C07C 21/18* (2013.01); *B01J 27/10* (2013.01); *C07C 17/04* (2013.01); *C07C 17/07* (2013.01); *C07C 19/10* (2013.01)

(58) Field of Classification Search
CPC ......... C09K 5/044; C07C 19/08; C07C 19/10; C07C 21/18
See application file for complete search history.

(56) References Cited

U.S. PATENT DOCUMENTS

| 10,577,296 B2 | 3/2020 | Sun et al. |
|---|---|---|
| 2002/0022753 A1 | 2/2002 | Drew et al. |
| 2010/0145111 A1 | 6/2010 | Sharratt et al. |
| 2011/0031436 A1* | 2/2011 | Mahler ................. C07C 17/087 252/78.1 |
| 2012/0053370 A1 | 3/2012 | Merkel et al. |
| 2014/0275648 A1 | 9/2014 | Chin et al. |
| 2014/0303409 A1 | 10/2014 | Wang et al. |
| 2014/0350309 A1 | 11/2014 | Wang et al. |
| 2015/0028246 A1 | 1/2015 | Mahler et al. |
| 2015/0183698 A1* | 7/2015 | Merkel ................. B01D 11/04 570/136 |
| 2017/0226035 A1 | 8/2017 | Deur-Bert et al. |
| 2020/0157025 A1 | 5/2020 | Sun et al. |
| 2020/0407293 A1 | 12/2020 | Wendlinger et al. |

FOREIGN PATENT DOCUMENTS

| CN | 1488614 A | 4/2004 | |
|---|---|---|---|
| CN | 103044191 A | 10/2014 | |
| JP | 2016519090 A | 6/2016 | |
| WO | 88/07031 A2 | 9/1988 | |
| WO | 2008/030440 A2 | 3/2008 | |
| WO | 2008/040969 A2 | 4/2008 | |
| WO | WO-2009105517 A2 * | 8/2009 | ........... C07C 17/386 |
| WO | 2009125199 A2 | 10/2009 | |
| WO | 2009137658 A2 | 11/2009 | |
| WO | 2015/095497 A1 | 6/2015 | |
| WO | 2016/156870 A1 | 10/2016 | |
| WO | 2017/013404 A1 | 1/2017 | |
| WO | 2017/044724 A1 | 3/2017 | |

OTHER PUBLICATIONS

International Search Report and Written Opinion for PCT/US2016/050918 dated Dec. 13, 2016.
International Search Report and Written Opinion for PCT/US2018/021867 dated Jun. 8, 2018.
PCT International Preliminary Report on Patentability in PCT/US2018/021867 dated Sep. 10, 2019.
Hazfldine R. N., Reactions of Fluorocarbon Radicals. Part V. Alternative Syntheses for Trifluoromethylacetylene (3:3:3-Trifluoropropyne), and the Influence of Polyfluoro-groups on Adjacent Hydrogen and Halogen Atoms, Journal of Chemical Society, 1951, pp. 2495-2504.

* cited by examiner

*Primary Examiner* — Jafar F Parsa

(57) ABSTRACT

The present application provides a process of preparing 3,3,3-trifluoroprop-1-ene, comprising reacting 3-chloro-1,1,1-trifluoropropane with a base in an aqueous solvent component in the absence of a phase transfer catalyst.

8 Claims, No Drawings

PROCESS FOR PREPARING 3,3,3-TRIFLUOROPROP-1-ENE

CROSS-REFERENCE TO RELATED APPLICATIONS

This application is a divisional of U.S. application Ser. No. 16/749,857, filed Jan. 22, 2020, which is a divisional application of U.S. application Ser. No. 15/917,376, filed Mar. 9, 2018, now issued as U.S. Pat. No. 10,577,295 on Mar. 3, 2020, which claims the benefit of U.S. Provisional Application Ser. No. 62/469,668, filed Mar. 10, 2017, the disclosure of each of which is incorporated herein by reference in its entirety.

TECHNICAL FIELD

The application relates to the preparation of 3,3,3-trifluoroprop-1-ene from 3-chloro-1,1,1-trifluoropropane in the presence of a base (e.g., an aqueous base) in an aqueous solvent component. The processes provided herein are conducted in the absence of a phase transfer catalyst.

BACKGROUND

Hydrofluoroolefins (HFOs), having low ozone depletion potential and low global warming potentials, are regarded as candidates for replacing saturated CFCs (chlorofluorocarbons) and HCFCs (hydrochlorofluorocarbons). HFOs can be employed in a wide range of applications, including their use as refrigerants, solvents, foam expansion agents, cleaning agents, aerosol propellants, dielectrics, fire extinguishants, and power cycle working fluids.

SUMMARY

The present disclosure provides a dehydrohalogenation process in the absence of organic solvents and dehydrohalogenation catalysts, including phase transfer catalysts. Accordingly, the present application provides a process of preparing 3,3,3-trifluoroprop-1-ene, comprising reacting 3-chloro-1,1,1-trifluoropropane with a base in an aqueous solvent component, wherein the reacting is conducted in the absence of a phase transfer catalyst. In some embodiments, the aqueous solvent component comprises 0 to 40% w/w of an organic solvent. In some embodiments, the aqueous solvent component does not comprise an organic solvent (i.e., the process is conducted in the absence of an organic solvent).

In another aspect, the present application further provides a process of preparing a mixture of 3,3,3-trifluoroprop-1-ene (HFO-1243zf) and 2-chloro-3,3,3-trifluoropropene (HCFO-1233xf), comprising reacting a mixture of 3-chloro-1,1,1-trifluoropropane (HCFC-253fb) and 1,1,1-trifluoro-2,3-dichloropropane (HCFC-243db) with a base in an aqueous solvent component, wherein the reacting is conducted in the absence of a phase transfer catalyst. In some embodiments, the aqueous solvent component comprises 0 to 40% of an organic solvent. In some embodiments, the aqueous solvent component does not comprise an organic solvent (i.e., the process is conducted in the absence of an organic solvent).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

DETAILED DESCRIPTION

Heretofore, phase transfer catalysts (PTCs) have been used to prepare HFOs. Although the PTCs accelerate the reactions, they also pose an environmental problem, as it is necessary to dispose of these spent catalysts. Further, the use of phase transfer catalysts increases the costs of dehydrohalogenation reactions, as well as adding complexity and cost to the work-up steps of the process as the catalyst needs to be separated from the organic and aqueous phases.

Eliminating the use of phase transfer catalysts and organic solvent components reduces the costs of these dehydrohalogenation reactions since they can be expensive. In addition, their elimination would make waste disposal easier and less expensive. Further, the elimination of phase transfer catalysts would simplify dehydrohalogenation reactions by reducing the need of recycling and recovering the catalysts from the process. Finally, because catalysts lower the activation energy of the dehydrohalogenation reactions, there is more of a tendency for the dehydrochlorinated product to break down and waste the starting material. Elimination of the phase transfer catalysts in the dehydrohalogenation reaction would reduce this risk. Thus, there is a need to conduct dehydrohalogenation reactions in the absence of phase transfer catalysts and organic solvent components in order to reduce costs and complexity of the process.

The foregoing general description and the following detailed description are exemplary and explanatory only and are not restrictive of the invention, as defined in the appended claims. Other features and benefits of any one or more of the embodiments will be apparent from the following detailed description, and from the claims.

Definitions and Abbreviations

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

As used herein, the term "consisting essentially of" is used to define a composition, method that includes materials, steps, features, components, or elements, in addition to those literally disclosed provided that these additional included materials, steps, features, components, or elements do not materially affect the basic and novel characteristic(s) of the claimed invention, especially the mode of action to achieve the desired result of any of the processes of the present invention. The term "consists essentially of" or "consisting essentially of" occupies a middle ground between "comprising" and "consisting of".

The term "alkyl", as used herein, either alone or in combination includes cyclic or acyclic and straight-chain or branched alkyl groups, such as, methyl, ethyl, n-propyl, i-propyl, or the different isomers thereof. For example, the alkyl group may contain 1-10 carbon atoms. The alkyl group may be a lower alkyl which contains from 1 to 6 carbon atoms.

"Aryl", as defined herein, whether used alone or in combination, refers to an aromatic ring containing 6, 10, 14, or 18 ring carbon atoms. Examples include phenyl, α-naphthyl, β-naphthyl, anthracenyl and the like.

By the use of the term "arylalkyl", it is meant that the alkyl group, as defined herein, is attached to the main chain at one end and aryl group on the other end. Examples include benzyl, phenethyl, phenpropyl and the like.

The term "heterocyclic", when used alone or in combination, refers to an aromatic, partially aromatic, partially saturated or saturated monocyclic, bicyclic or tricyclic ring system containing 3 to 14 ring atoms, in which 1, 2, or 3 of the ring atoms are independently selected from nitrogen, oxygen and sulfur and the remaining ring atoms are carbon atoms. The heterocyclic ring may be completely heteroaromatic or partly heteroaromatic, in which one of the rings fused to the heterocyclic ring is aromatic. Thus, heterocyclic, as used herein, includes heteroaromatic. In addition, the heterocyclic ring may contain one or more double bonds, either between two carbons, between two nitrogen atoms or between a nitrogen atom and a carbon atom. The designation of the aza, oxa or thio as a prefix before heterocyclyl define that at least a nitrogen, oxygen or sulfur atom is present, respectively, as a ring atom. The nitrogen atom of a heterocyclic compound may be a basic nitrogen atom. The nitrogen or sulfur atom of the heterocyclic compound may also be optionally oxidized to the corresponding N-oxide, S-oxide or S,S-dioxide. When a heteroaryl is substituted by a hydroxy group, it also includes its corresponding tautomer. Exemplary heterocyclic includes piperidyl, pyrrolidinyl, piperazinyl, morpholinyl, tetrahydrofuryl, thiomorpholinyl, thiazolidinyl, 1,3-dioxolanyl, 1,4-dioxanyl, tetrahydrothiophenyl, tetrahydrothiopyranyl. pyrazinyl, thienyl, isothiazolyl, oxazolyl, pyrazolyl, furanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofuranyl, azaindolyl, benzimidazolyl, benzothienyl, thienopyridyl, thienopyrimidyl, pyrrolopyridyl, imidazopyridyl, benzoazaindolyl, 1,2,4-triazinyl, benzothiazolyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, and triazolyl and the like.

The term "halogen" refers to fluoro, chloro, bromo and iodo.

The term "dehydrohalogenation", as used herein, means a process during which hydrogen and halogen, e.g. Cl, Br or I on adjacent carbons in a molecule are removed to form the corresponding olefin.

As used herein, the term "dehydrochlorination" refers to a process during which hydrogen and chlorine on adjacent carbons in a molecule are removed to form the corresponding olefin.

The term "aqueous solvent" refers to a solvent comprised of water or a mixture of one or more solvents mixed with water. In some embodiments, water is the sole solvent. However, the aqueous solvent may also comprise water mixed with a polar solvent, such as methanol, ethanol 1-propanol, 2-propanol, 1,3-butandiol, 1,2-butanediol, acetonitrile, acetaldehyde, acetone, ethylene glycol, propylene glycol, tetrahydrofuran, triethylene glycol, 1,3-propanediol, glycerol, 1,4 dioxane, and the like.

The term "mixing", as defined herein, refers to the process of stirring the reactants (e.g., 3-chloro-1,1,1-trifluoropropane and base), at a particular mixing power of, for example, about 0.1 to about 50 horsepower per 1000 gallons of the reaction mixture (e.g., an aqueous reaction mixture). The stirring (i.e., mixing) can be effected, for example, by mechanical means (e.g., a stirrer or in a shaker so that the reactants are substantially thoroughly mixed with one another under conditions sufficient to dehydrohalogenate the 3-chloro-1,1,1-trifluoropropane to produce 3,3,3-trifluoroprop-1-ene) and by other means known in the art or as described herein.

Accordingly, in some embodiments, mixing is provided by a mechanical agitator. However the mixing power input can alternatively be provided by other methods. These methods are known in the industry and include using the mixing provided by gas bubbles from gas added to the vessel or generated within the vessel by vaporization of liquid. Mixing can also be provided by withdrawing the liquid from the vessel to a pump and pumping the liquid back into the vessel. A static mixer, rotor stator heads, or other device intended to mix the contents can be present in the circulation path of the liquid to provide additional mixing power input. Mixing can be provided by a single method or by a combination of two or more methods.

In some embodiments, the reactor stirs the reaction mixture (e.g., 3-chloro-1,1,1-trifluoropropane and base, and amine if present) by imparting to the agitator the power to stir the liquid in the tank. The power input is calculated based on the combination of several parameters, including the geometry of the vessel, design of baffles, if any, design of the impeller, and speed at which the impeller rotates. This calculation is performed by one of ordinary skill in the art. In the process described herein, to maximize the yield, in an embodiment the base are mixed together, generating small bubbles and high interphase surface area. Autoclave reactors are examples of reactors that could achieve the above-identified horsepower per gallon of liquid. In an embodiment, about 0.1 to about 50 horsepower/1000 gallon of liquid is imparted to the agitator, making the agitator agitate the reaction mixture, while in another embodiment, about 0.5 to about 40 horsepower/1000 gallon of liquid is imparted to the agitator, making the agitator agitate the reaction mixture, and another embodiment, about 1 to about 35 horsepower/1000 gallon of liquid is imparted to the agitator, causing the agitator to agitate the reaction mixture.

As used herein, "caustic" refers to a base that would dissociate when placed in water. Examples include an alkali metal oxides, hydroxide, or amide, such as sodium or potassium oxide or sodium or potassium hydroxide or sodium or potassium amide; or alkaline earth metal hydroxide, alkaline earth metal oxide or amide, alkali metal carbonate or alkali metal phosphate or alkali metal carboxylate.

The process of the present reaction, in an embodiment, is carried out in the presence of a base that would dissociate when placed in water. Examples include metal oxides, hydroxides, amides, carbonates, phosphates or carboxylates. However, as defined the term "base" excludes amines, including ammonia. Unless indicated to the contrary, the term "amine" includes ammonia.

As used herein, "metal" in the terms—metal hydroxide base, metal carbonate base, a metal phosphate base, or a metal fluoride base—refers to an alkali metal or alkaline earth metal.

As used herein, by the term "alkali metal hydroxide", refers to a compound or mixture of compounds selected from the group consisting of lithium hydroxide, sodium hydroxide, potassium hydroxide, rubidium hydroxide and cesium hydroxide. In some embodiments, the alkali metal hydroxide is sodium hydroxide.

As used herein, the term "alkali metal amide", refers to a compound or mixture of compounds selected from the group consisting of lithium amide, sodium amide, potassium amide, rubidium amide, and cesium amide.

As used herein, the term "alkaline earth metal hydroxide", refers to a compound or mixture of compounds selected from the group consisting of beryllium hydroxide, magnesium hydroxide, calcium hydroxide, strontium hydroxide, and barium hydroxide.

As used herein, the term "alkaline earth metal amide" refers to a compound or mixture of compounds selected from the group consisting of beryllium amide, magnesium amide, calcium amide, strontium amide, and barium amide.

As used herein, the term "alkali metal carbonate", refers to a compound or mixture of compounds selected from the group consisting of lithium carbonate, sodium carbonate, potassium carbonate, rubidium carbonate, and cesium carbonate.

As used herein, the term "alkaline earth metal carbonate" refers to a compound or mixture of compounds selected from the group consisting of beryllium carbonate, magnesium carbonate, calcium carbonate, strontium carbonate, and barium carbonate.

As used herein, the term "alkali metal oxide", refers to a compound or mixture of compounds selected from the group consisting of lithium oxide, sodium oxide, potassium oxide, rubidium oxide, and cesium oxide.

As used herein, the term "alkaline earth metal oxide" refers to a compound or mixture of compounds selected from the group consisting of beryllium oxide, magnesium oxide, calcium oxide, strontium oxide, and barium oxide.

As used herein, the term "alkali metal phosphate", refers to a compound or mixture of compounds selected from the group consisting of lithium phosphate, sodium phosphate, potassium phosphate, rubidium phosphate, and cesium phosphate.

As used herein, the term "alkaline earth metal phosphate" refers to a compound or mixture of compounds selected from the group consisting of beryllium phosphate, magnesium phosphate, calcium phosphate, strontium phosphate, and barium phosphate.

In an embodiment, an amine or ammonia is additionally present. The dehydrohalogenation reaction, in an embodiment, is conducted in the presence of the base described hereinabove and an amine of the formula R1R2R3N, wherein R1, R2, and R3 are as defined hereinabove. The alkyl group, heterocyclic group, aryl group, aralkyl group, and the heterocyclicalkyl group of R1, R2 and R3 can be substituted or unsubstituted. Substituted alkyl group, substituted heterocyclic group, substituted aryl group, substituted aralkyl group or substituted heterocyclicalkyl herein means that one or more hydrogens on carbon atoms have been substituted by functional groups, such as hydroxyl groups, alkoxy groups, halogens, amino groups, and the like. The amine, as defined herein, can be aliphatic amine, aromatic amine, or heterocyclic amine or mixtures thereof. In some embodiments, the amine is an aliphatic amine.

In some embodiments, when present, the amine can be primary amine, secondary amine, tertiary amine, or mixtures thereof. In some embodiments, the amine is a primary unsubstituted alkyl amine of the formula $RNH_2$ wherein R is a $C_1$-$C_{16}$ unsubstituted alkyl group. In some embodiments, the amine is primary unsubstituted alkyl amine of the formula $R1NH_2$ wherein R1 is a $C_1$-$C_3$ unsubstituted alkyl group. Examples of primary unsubstituted alkyl amines include methylamine, ethylamine, propylamine, isopropylamine, butylamine, sec-butylamine, tert-butylamine, amylamine, isoamylamine, tert-amylamine, hexylamine, and mixtures thereof.

In some embodiments, when present, the amine is secondary unsubstituted alkyl amine of the formula R1R2NH wherein each R1 and R2 is independently a $C_1$-$C_6$ unsubstituted alkyl group. In some embodiments, the amine is secondary unsubstituted alkyl amine of the formula R1R2NH wherein each R is independently a $C_1$-$C_3$ unsubstituted alkyl group. Examples of secondary unsubstituted alkyl amines include dimethylamine, diethylamine, dipropylamine, diisopropylamine, dibutylamine, di-sec-butylamine, diamylamine, dihexylamine, and mixtures thereof.

In some embodiments, the amine is tertiary unsubstituted alkyl amine of the formula R1R2R3N wherein each R1, R2 and R3 is independently a $C_1$-$C_6$ unsubstituted alkyl group. In some embodiments, when present, the amine is tertiary unsubstituted alkyl amine of the formula R1R2R3N wherein each R1, R2 and R3 is independently a $C_1$-$C_3$ unsubstituted alkyl group. Examples of tertiary unsubstituted alkyl amines include trimethylamine, triethylamine, tripropylamine, tributylamine, triamylamine, trihexylamine, N,N-dimethylethylamine, N,N-dimethylpropylamine, N,N-dimethylbutylamine, and mixtures thereof.

In other embodiments, when present, the amine is selected from the group consisting of methylamine, dimethylamine, trimethylamine, ethylamine, diethylamine, triethylamine, propylamine, isopropylamine, dipropylamine, diisopropylamine, tripropylamine, butylamine, sec-butylamine, tert-butylamine, dibutylamine, tributylamine, di-sec-butylamine, amylamine, isoamylamine, tert-amylamine, diamylamine, triamylamine, hexylamine, dihexylamine, trihexylamine, 1,1,3,3-tetramethylbutylamine), N,N-dimethylethylamine, N,N-dimethylpropylamine, N,N-dimethylbutylamine, and mixtures thereof.

In other embodiments, the amine has one or two or three substituted alkyl groups thereon, which may be the same or different wherein one or more hydrogens on carbon atoms have been substituted by hydroxyl groups. Examples of such amine include ethanolamine ($H_2NCH_2CH_2OH$), diethanolamine, triethanolamine, tris(hydroxymethyl)aminomethane (($HOCH_2$)$_3CNH_2$), 2-(methylamino)ethanol ($CH_3NHCH_2CH_2OH$), 2-(ethylamino)ethanol ($CH_3CH_2NHCH_2CH_2OH$), 2-(propylamino)ethanol ($CH_3CH_2CH_2NHCH_2CH_2OH$), 2-(isopropylamino)ethanol (($CH_3$)$_2CHNHCH_2CH_2OH$), 2-(butylamino)ethanol ($CH_3(CH_2)_3NHCH_2CH_2OH$), 2-(tert-butylamino)ethanol (($CH_3$)$_3CNHCH_2CH_2OH$), triisopropanolamine ([$CH_3CH$ (OH)CH$_2$]$_3$N), N,N-dimethylethanolamine (HOCH$_2$CH$_2$N(CH$_3$)$_2$), 1-dimethylamino-2-propanol ((CH$_3$)$_2$NCH$_2$CH(OH)CH$_3$), 3-dimethylamino-1-propanol ((CH$_3$)$_2$N(CH$_2$)$_3$OH), 2-amino-2-methyl-1-propanol ((CH$_3$)$_2$C(NH$_2$)CH$_2$OH), and mixtures thereof.

In still other embodiments, one of R1, R2 and R3 of the amine has a $C_1$-$C_6$ substituted alkyl group thereon wherein one or more hydrogens on carbon atoms have been substituted by hydroxyl groups, and the remaining groups are independently selected from the group consisting of hydrogen and $C_1$-$C_{16}$ unsubstituted alkyl groups. Examples of such amine include ethanolamine (H$_2$NCH$_2$CH$_2$OH), tris(hydroxymethyl)aminomethane ((HOCH$_2$)$_3$CNH$_2$), 2-(methylamino)ethanol (CH$_3$NHCH$_2$CH$_2$OH), 2-(ethylamino)ethanol (CH$_3$CH$_2$NHCH$_2$CH$_2$OH), 2-(propylamino)ethanol (CH$_3$CH$_2$CH$_2$NHCH$_2$CH$_2$OH), 2-(isopropylamino)ethanol ((CH$_3$)$_2$CHNHCH$_2$CH$_2$OH), 2-(butylamino)ethanol (CH$_3$(CH$_2$)$_3$NHCH$_2$CH$_2$OH), 2-(tert-butylamino)ethanol ((CH$_3$)$_3$CNHCH$_2$CH$_2$OH), N,N-dimethylethanolamine (HOCH$_2$CH$_2$N(CH$_3$)$_2$), 1-dimethylamino-2-propanol ((CH$_3$)$_2$NCH$_2$CH(OH)CH$_3$), 3-dimethylamino-1-propanol ((CH$_3$)$_2$N(CH$_2$)$_{30}$H), 2-amino-2-methyl-1-propanol ((CH$_3$)$_2$C(NH$_2$)CH$_2$OH), and mixtures thereof. In some embodiments, at least one R1, R2 and R3 group of the amine is a $C_1$-$C_6$ substituted alkyl group wherein one or more hydrogens on carbon atoms have been substituted by amino groups, and the rest of the groups, are independently selected from the group consisting of hydrogen and $C_1$-$C_{16}$ unsubstituted alkyl groups. Examples of such amines include 3-(dimethylamino)propylamine ((CH$_3$)$_2$N(CH$_2$)$_3$NH$_2$), 3-(diethylamino)propylamine ((C$_2$H$_5$)$_2$N(CH$_2$)$_3$NH$_2$), and mixtures thereof.

In some embodiments, when present, the amine is polyamine. Examples of polyamines include ethylene diamine, 1,2-propylenediamine, 1,3-propylenediamine, 1,4-diaminobutane, 1,3-diaminopentane, 1,5-diaminopentane, 1,6-diaminohexane, 2-methyl-1,5-pentanediamine, spermidine (N-(3-aminopropyl)butane-1,4-diamine), spermine (N,N'-bis(3-aminopropyl)butane-1,4-diamine), diethylenetriamine, triethylenetetramine, and mixtures thereof.

In some embodiments, the amine, when present is heterocyclic amine. Examples of heterocyclic amines include pyrrolidine, pyrroline (including 1-pyrroline, 2-pyrroline and 3-pyrroline), piperidine, piperazine, morpholine, imidazole, pyrazole, pyridine, pyrimidine, pyridazine, pyrazine, pyridine, bipyridine (including 2,2'-bipyridine, 4,4'-bipyridine, 2,3'-bipyridine, and 3,4'-bipyridine, etc.), and mixtures thereof.

In other embodiments, the amine, when present, is hydrazine (NH$_2$NH$_2$), hydrazine derivatives, such as alkyl hydrazines or arylhydrazines or aralkyl hydrazines and the like and mixtures thereof. Examples of hydrazine derivatives include methylhydrazine (CH$_3$NHNH$_2$), 1,1-dimethylhydrazine ((CH$_3$)$_2$NNH$_2$), 1,2-dimethylhydrazine (CH$_3$NHNHCH$_3$), phenylhydrazine, 2,4-dinitrophenylhydrazine, and mixtures thereof.

In some embodiments, the amine, when present, is an aromatic amine. Examples of aromatic amines include aniline, o-toluidine, m-toluidine, p-toluidine, xylidine, 2,4,6-trimethylaniline, o-anisidine, m-anisidine, p-anisidine, N-methylaniline, N,N-dimethylaniline, N-ethylaniline, N,N-diethylaniline, and mixtures thereof.

In an embodiment, mixtures of any of the aforementioned amines may also be used in this disclosure.

In some embodiments, the amine, when present, is selected from the group consisting of heterocyclic amines, hydrazine and its derivatives, and mixtures thereof. In some embodiments, the amine is a heterocyclic amine, and mixtures thereof.

In an embodiment, one of R1, R2 and R3 is hydrogen and the other of R1, R2 and R3 are independently lower alkyls. In an embodiment, R2 and R3 may be the same or different. In another embodiment, R1, R2 and R3 are the same or different and other than hydrogen. For example, R1, and R2 and R3 are independently lower alkyls. In still another embodiment, R1 is phenyl, alkyl, pyridine, alkyl substituted pyridine and R2 and R3 are as defined hereinabove. In another embodiment, the amine is hydrazine.

In an embodiment, the amine, when present, is trialkyl or dialkyl amine and preferred amines are trialkylamine.

It should be noted that all combinations and permutations of R1, R2, and R3 are contemplated.

In an embodiment, the mole ratio of amine, when present, to halofluoroalkane ranges from about 0.02 to about 3. In one embodiment, the mole ratio ranges from about 0.05 to about 0.5, and in another embodiment, the mole ratio ranges from about 0.05 to about 0.25.

In addition, in an embodiment, the mole ratio of amine, when present, to base ranges from about 0.05 to about 3, and in another embodiment, from about 0.05 to about 1, and in a still further embodiment, from about 0.05 to about 0.5.

As described herein, the processes of the present application are conducted in the absence of a catalyst. As used herein, the term "catalyst", refers to a substance that speeds up the chemical reaction, but is not consumed by the reaction; thus it can be recovered chemically unchanged at the end of the reaction. A phase transfer catalyst is a heterogenous catalyst that facilitates the migration of a reactant from one phase into another phase where the reaction occurs. For example, a phase transfer catalyst is a catalyst which facilitates the transfer of an ionic compound into an organic phase from, for example, a water phase. If water is used as a solvent, an aqueous or inorganic phase is present as a consequence of the base (e.g., alkali metal hydroxide) and an organic phase is present as a result of the (chloro)fluorocarbon. The phase transfer catalyst facilitates the reaction of these dissimilar components. While various phase transfer catalysts may function in different ways, their mechanism of action is not determinative of their utility in the present invention provided that they facilitate the dehydrohalogenation reaction. For example, the processes provided herein may be conducted in the absence of a phase transfer catalyst which is ionic or neutral. In some embodiments, the processes provided herein are conducted in the absence of a phase transfer catalyst selected from the group consisting of crown ethers, onium salts, cryptands, and polyalkylene glycols and derivatives thereof (e.g., fluorinated derivatives thereof). In some embodiments, process provided herein is conducted in the absence of a phase transfer catalyst provided in International Patent Application No. PCT/US2016/050918, the disclosure of which is incorporated herein by reference in its entirety.

Derivatives of the above crown ethers are considered phase transfer catalysts such as dibenzyl-18-crown-6, dicyclohexanyl-18-crown-6, dibenzyl-24-crown-8 and dibenzyl-12-crown-4, are also excluded. Other compounds analogous to the crown ethers which differ by the replacement of one or more of the oxygen atoms by other kinds of donor atoms, particularly N or S are also excluded. In addition, fluorinated derivatives, such as compounds in which one or more of the hydrogen atoms are substituted by fluorine, are excluded as well.

Cryptands are another class of compounds that are excluded. These are three dimensional polymacrocyclic chelating agents that are formed by joining bridgehead structures with chains that contain properly spaced donor atoms. The donor atoms of the bridges may all be O, N, or S, or the compounds may be mixed donor macrocycles in which the bridge strands contain combinations of such donor atoms. For example, cryptands which include bicyclic molecules that result from joining nitrogen bridgeheads with chains of (—OCH$_2$CH$_2$—) groups, for example as in [2.2.2] cryptand (4,7,13,16,21,24-hexaoxa-1,10-diazabicyclo[8.8.8]hexacosane, available under the brand names Kryptand 222 and Kryptofix 222), are excluded.

Onium salts of any kind, including quaternary phosphonium salts and quaternary ammonium salts, useful as catalysts, are excluded. Specific examples of such phosphonium salts and quaternary ammonium salts which are excluded include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulphate, tetra-n-butylphosphonium chloride, tetraphenylphosphonium bromide, tetraphenylphosphonium chloride, triphenylmethylphosphonium bromide and triphenylmethylphosphonium chloride and benzyltriethylammonium chloride are excluded.

Other onium salts which exhibit high temperature stabilities (e.g. up to about 200° C.), for example, 4-dialkylaminopyridinium salts, tetraphenylarsonium chloride, bis [tris(dimethylamino)phosphine] iminium chloride and tetrakis[tris(dimethylamino) phosphinimino] phosphonium chloride are also excluded.

Polyalkylene glycol compounds useful as phase transfer catalysts are also excluded. For example, polyalkylene glycol compounds represented by the formula $R^6O(R^5O)_mR^7$ wherein $R^5$ is a $C_{1-10}$ alkylene group, each of $R^6$ and $R^7$ are, independently H, $C_{1-10}$alkyl group, an aryl group,(i.e., an aromatic group containing 6, 10 or 14 ring carbon atoms or heteroaryl group containing 5 to 14 ring atoms and 1 to 3 heteroatoms selected from N, O and S and the remainder ring atoms are carbon atoms, e.g., phenyl, naphthyl or pyridinyl) or an arylalkyl group (e.g. benzyl or $C_{1-10}$ alkyl-substituted phenyl), and m is an integer of at least 2 are also excluded. Such polyalkylene glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, monoalkyl glycol ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers of such glycols, and polyalkylene glycols such as polyethylene glycol (average molecular weight about 300) and polyethylene glycol (average molecular weight about 400) and the dialkyl (e.g. dimethyl, dipropyl, dibutyl)ethers of such polyalkylene glycols are excluded.

The following abbreviations may be used throughout the present application:

CFC: chlorofluorocarbon
HFO: hydrofluoroolefin
HCFC: hydrochlorofluorocarbon
HFO-1243zf (i.e., 1243zf): 3,3,3-trifluoroprop-1-ene
HFO-1234yf (i.e., 1234yf): 2,3,3,3-tetrafluoroprop-1-ene
HCFC-243db: 1,1,1-trifluoro-2,3-dichloropropane
HCFC-244bb: 2-chloro-1,1,1,2-tetrafluoropropane
HCFC-253fb (i.e., 2531b): 3-chloro-1,1,1-trifluoropropane
HCFO-1233xf (i.e., 1233xf): 2-chloro-3,3,3-trifluoroprop-1-ene
HFC-254fb: (i.e., 254fb): 1,1,1,3-tetrafluoropropane
HFC-245cb: 1,1,1,2,2-pentafluoropropane
PTC: phase transfer catalyst
psig: pounds per square inch gauge
RPM: revolutions per minute
Process of Preparing 3,3,3-Trifluoroprop-1-ene Accordingly, the present application provides a process of preparing 3,3,3-trifluoroprop-1-ene (i.e., "HFO-1243zf" or "1243zf") comprising reacting 3-chloro-1,1,1-trifluoropropane (i.e., "HCFC-253fb" or "253fb") with a base, wherein the reacting is conducted in the absence of a phase transfer catalyst. A schematic representation of the process provided herein is shown below in Scheme 1.

Scheme 1.

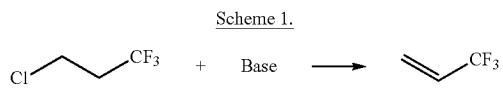

Because phase transfer catalysts (e.g., dehydrohalogenation catalysts such as dehydrochlorination catalysts) are not used in the processes described herein, the costs of the reactions are minimized, as these catalysts can be expensive. These catalysts need to be separated from the product and are difficult to dispose, which adds additional expense to a catalyzed system. The process provided herein, which is conducted in the absence of catalysts, does not have this added expense. Further, the elimination of phase transfer catalysts simplifies the dehydrohalogenation reaction by reducing the need of recycling and recovering these catalysts from the process. Finally, since the catalysts lower the activation energy of the dehydrohalogenation reactions, and since there is more of a tendency for the dehydrohalogenated product to break down and waste the starting material, elimination of the phase transfer catalysts in the dehydrohalogenation reaction reduces this risk.

In some embodiments, the reacting is conducted in the absence of a phase transfer catalyst. In some embodiments, the reacting is conducted in an aqueous solvent component. In some embodiments, the reacting is conducted in an aqueous solvent component and in the absence of a phase transfer catalyst. In some embodiments, the reacting is conducted in water and in the absence of a phase transfer catalyst.

In some embodiments, the reacting is conducted in the absence of a phase transfer catalyst and the aqueous solvent component comprise 0 to 40% w/w of an organic solvent. In some embodiments, the reacting is conducted in the absence of a phase transfer catalyst and the aqueous solvent component comprises 0 to 30% w/w of an organic solvent. In some embodiments, the reacting is conducted in the absence of a phase transfer catalyst and the aqueous solvent component comprises 0 to 20% w/w of an organic solvent. In some embodiments, the reacting is conducted in the absence of a phase transfer catalyst and the aqueous solvent component comprises 0 to 10% w/w of an organic solvent. In some embodiments, the reacting is conducted in the absence of a phase transfer catalyst and the aqueous solvent component does not comprise an organic solvent. In some embodiments, the reacting is conducted in the absence of a phase transfer catalyst and an organic solvent. In some embodiments, the reacting is conducted in the absence of a phase transfer catalyst and an organic solvent component selected from an aliphatic alcohol, such as methanol, ethanol, n-propanol, isopropanol, butanol, and the like.

In some embodiments, the reacting is conducted as a liquid phase reaction. In some embodiments, the reacting is performed in the presence of water.

Exemplary bases useful in the processes provided herein include metal bases such as metal oxides (e.g., alkali metal oxides or alkaline earth metal oxides), metal hydroxides (e.g., alkali metal hydroxides or alkaline earth metal hydroxides), metal amides (e.g., alkali metal amides or alkaline earth metal amides), metal carbonates (e.g. alkali metal carbonates or alkaline earth metal carbonates), or metal phosphates (e.g., alkali metal phosphates or alkaline earth metal phosphates. In some embodiments, the metal base is a transition metal base (e.g., zinc hydroxide). Exemplary metals included in the metal bases provided herein include, but are not limited to, sodium, potassium, lithium, cesium, calcium, zinc, and the like.

In some embodiments, the base is an alkali metal hydroxide.

In some embodiments, the base is mixed with water to form an aqueous base (e.g., an aqueous basic suspension) or an aqueous basic solution. In some embodiments, the base is an aqueous base.

In some embodiments, the base is a metal hydroxide base, a metal carbonate base, a metal phosphate base, or a metal fluoride base.

In some embodiments, the base is an alkali metal hydroxide base, an alkaline earth metal hydroxide base, an alkali metal carbonate base, an alkali metal phosphate base, or an alkali metal fluoride base.

In some embodiments, the base is an alkali metal hydroxide base.

In some embodiments, the base is NaOH, KOH, LiOH, CsOH, Ca(OH)$_2$, Zn(OH)$_2$, Na$_2$CO$_3$, K$_2$CO$_3$, K$_3$PO$_4$, Na$_3$PO$_4$, KF, or CSF.

Preferably, the base is KOH or NaOH.

In some embodiments, the base is NaOH.

In some embodiments, the base is KOH.

In some embodiments, the base is aqueous NaOH.

In some embodiments, the base is aqueous KOH.

In some embodiments, about 0.5 to about 10 molar equivalents of base is used based on one molar equivalent of 3-chloro-1,1,1-trifluoropropane. In some embodiments, about 1 to about 2 molar equivalents of base is used based on one molar equivalent of 3-chloro-1,1,1-trifluoropropane. In some embodiments, about 0.01 to about 5 molar equivalents of base is used based on one molar equivalent of 3-chloro-1,1,1-trifluoropropane. In some embodiments, about 0.02 to about 4 molar equivalents of base is used based on one molar equivalent of 3-chloro-1,1,1-trifluoropropane. In some embodiments, about 0.02 to about 2 molar equivalents of base is used based on one molar equivalent of 3-chloro-1,1,1-trifluoropropane. In some embodiments, about 0.05 to about 1.5 molar equivalents of base is used based on one molar equivalent of 3-chloro-1,1,1-trifluoropropane.

In some embodiments, the reacting is conducted at a temperature of from about 20° C. to about 100° C., for example, about 20° C. to about 100° C., about 20° C. to about 80° C., about 20° C. to about 60° C., about 20° C. to about 40° C., about 20° C. to about 30° C., about 30° C. to about 100° C., about 30° C. to about 80° C., about 30° C. to about 60° C., about 30° C. to about 40° C., about 40° C. to about 100 C, about 40° C. to about 80° C., about 40° C. to about 60° C., about 60° C. to about 100° C., about 60° C. to about 80° C., or about 80° C. to about 100° C.

In some embodiments, the reacting is conducted at a temperature of from about 35° C. to about 80° C.

In some embodiments, the reacting is conducted at a temperature of from about 35° C. to about 65° C.

In some embodiments, the reacting is conducted at a temperature of from about 55° C. to about 65° C.

In some embodiments, the reacting is conducted at a temperature of from about 30° C. to about 40° C.

In some embodiments, the reacting is conducted at a pressure of about −10 psig to about 500 psig. In some embodiments, the reacting is conducted at a pressure of −10 psig to about 230 psig, for example, −10 psig to about 230 psig, −10 psig to about 150 psig, −10 psig to about 125 psig, −10 psig to about 100 psig, −10 psig to about 75 psig, −10 psig to about 50 psig, −10 psig to about 25 psig, −10 psig to about 0 psig, 0 psig to about 150 psig, 0 psig to about 125 psig, 0 psig to about 100 psig, 0 psig to about 75 psig, 0 psig to about 50 psig, 0 psig to about 25 psig, 25 psig to about 150 psig, 25 psig to about 125 psig, 25 psig to about 100 psig, 25 psig to about 75 psig, 25 psig to about 50 psig, 50 psig to about 150 psig, 50 psig to about 125 psig, 50 psig to about 100 psig, 50 psig to about 75 psig, 75 psig to about 150 psig, 75 psig to about 125 psig, 75 psig to about 100 psig, 100 psig to about 150 psig, 100 psig to about 125 psig, or 125 psig to about 150 psig.

In some embodiments, the reacting is conducted at a pressure of about 5 psig to about 230 psig.

In some embodiments, the reacting is conducted at a pressure of about 5 psig to about 150 psig.

In some embodiments, the reacting comprises mixing the 3-chloro-1,1,1-trifluoropropane and base with a mixing power of from about 0.1 to about 50 horsepower per 1000 gallons of the reaction mixture, for example, about 0.1 to about 50, about 0.1 to about 40, about 0.1 to about 30, about 0.1 to about 20, about 0.1 to about 10, about 0.1 to about 1, about 1 to about 50, about 1 to about 40, about 1 to about 30, about 1 to about 20, about 1 to about 10, about 10 to about 50, about 10 to about 40, about 10 to about 30, about 10 to about 20, about 20 to about 50, about 20 to about 40, about 20 to about 30, about 30 to about 50, about 30 to about 40, or about 40 to about 50 horsepower per 1000 gallons of the reaction mixture.

In some embodiments, the reacting comprises stirring the 3-chloro-1,1,1-trifluoropropane and base with a mixing power of from about 0.5 to about 40 horsepower per 1000 gallons of the reaction mixture.

In some embodiments, the reacting comprises stirring the 3-chloro-1,1,1-trifluoropropane and base with a mixing power of from about 1 to about 35 horsepower per 1000 gallons of the reaction mixture.

In some embodiments, the reacting is conducted at a temperature of from about 35° C. to about 80° C. and at a pressure of about 5 psig to about 230 psig.

In some embodiments, the reacting is conducted at a temperature of from about 55° C. to about 80° C. and at a pressure of about 5 psig to about 230 psig.

In some embodiments, the reacting is conducted at a temperature of from about 35° C. to about 80° C. and at a pressure of about 5 psig to about 150 psig.

In some embodiments, the reacting is conducted at a temperature of from about 30° C. to about 80° C. and at a pressure of about 5 psig to about 150 psig.

The present application further provides a process of preparing 3,3,3-trifluoroprop-1-ene, comprising reacting 3-chloro-1,1,1-trifluoropropane with aqueous NaOH, wherein the reacting is performed at a temperature of from about 35° C. to about 80° C. and at a pressure of from about 5 psig to about 150 psig, and wherein the reacting is conducted in the absence of a phase transfer catalyst and an organic solvent component.

In some embodiments, the reacting is conducted at a pressure of from about 5 psig to about 150 psig.

In some embodiments, the 3-chloro-1,1,1-trifluoropropane is prepared by reacting 1,1,1,3-tetrachloropropane with hydrofluoric acid. In some embodiments, the 3-chloro-1,1,1-trifluoropropane is produced as a byproduct, intermediate, or coproduct during a process of preparing HFO-1243zf.

In some embodiments, the 3-chloro-1,1,1-trifluoropropane is prepared by reacting 1,1,1-trifluoropropane with $Cl_2$.

The process described herein, in the presence or absence of an amine, may be conducted in the presence of an inert gas such as He, Ar, or $N_2$. In some embodiments, the inert gas is co-fed into the reactor with the starting material.

In an embodiment, the process, described herein, in the presence or absence of an amine, is conducted in the liquid phase an aqueous solvent using well-known chemical engineering practice, such as a continuous process, batch process, semi-continuous process or a combination thereof.

Under the conditions described, and in all cases of a continuous, batch, or semi-continuous operation, the reaction is completed a relatively short time after initiated. In an embodiment, a reaction time up to about 4 hours is sufficient. For example, in an embodiment, the reaction time ranges from about 1 to about 120 minutes, while in another embodiment, the reaction time ranges from about 3 to about 60 minutes and in another embodiment, from about 5 to about 30 minutes.

The 3,3,3-trifluoroprop-1-ene is isolated using separation techniques known in the art, such as distillation, chromatography, extraction and the like. In some embodiments, the 3,3,3-trifluoroprop-1-ene can be isolated by distillation directly from the reaction vessel.

The 3,3,3-trifluoroprop-1-ene can be used to prepare further compounds, including HFO-1234yf, which is useful for a variety of applications. Accordingly, in some embodiments, the process of further comprises reacting the 3,3,3-trifluoroprop-1-ene with chlorine to make 2,3-dichloro-1,1,1-trifluoropropane (HCFC-243db), followed by dehydrochlorination to form 2-chlorine-3,3,3-trifluoropropene (HCFO-1233xf), followed by reaction with HF to form 2-chloro-1,1,1,2-tetrafluoropropane (HCFC-244bb), and finally dehydrochlorination to form 2,3,3,3-tetrafluoropropene (HFO-1234yf).

In some embodiments, the present application further provides chlorinating 3,3,3-trifluoropropene to form 1,1,1-trifluoro-2,3-dichloropropane (HCFC-243db). In some embodiments, chlorinating comprises reacting with chlorine or HCl/oxygen.

In some embodiments, the process of preparing HCFC-243db is that disclosed in WO 2015095497, which is incorporated herein by reference in its entirety.

Accordingly, in some embodiments, the process further comprises contacting 3,3,3-trifluoropropene with chlorine in the liquid phase, in the absence or presence of a catalyst and with or without exposure to UV light, to form 1,1,1-trifluoro-2,3-dichloropropane (HCFC-243db).

In some embodiments, the catalyst comprises at least one metal halide, wherein the metal is a metal from Group 13, 14 or 15 of the periodic table or a transition metal or combination thereof. In some embodiments, the metal halide is supported on activated carbon. In some embodiments, the activated carbon is acid washed or caustic washed. In some embodiments, the metal is nickel, chromium, iron, scandium, yttrium, lanthanum, titanium, zirconium, hafnium, vanadium, molybdenum, tungsten, manganese, rhenium, ruthenium, osmium, cobalt, palladium, copper, zinc, tantalum, aluminum, tin, or lead. In some embodiments, the metal halide is nickel halide, iron halide or chromium halide. In some embodiments, the halide is a chloride. In some embodiments, the metal halide is nickel chloride, iron halide or chromium halide.

In some embodiments, the chlorination occurs in the vapor phase with or without a catalyst. In some embodiments, the chlorination is conducted at a temperature ranging from about 80° C. to about 200° C. and a pressure ranging from about 10 psig to about 100 psig, with the mole ratio of 3,3,3-trifluoropropene to chlorine gas ranging from about 1:0.02 to about 1:1.

The present application further provides a process of preparing 2-chloro-3,3,3-trifluoropropene (HCFO-1233xf), comprising dehydrochlorinating 1,1,1-trifluoro-2,3-dichloropropane (HCFC-243db) to form 2-chloro-3,3,3-trifluoropropene (HCFO-1233xf).

The present application also provides a process of preparing 2-chloro-3,3,3-trifluoropropene (HCFO-1233xf), comprising reacting 1,1,1-trifluoro-2,3-dichloropropane (HCFC-243db) with caustic to form 2-chloro-3,3,3-trifluoropropene (HCFO-1233xf).

In some embodiments, the process of preparing HCFO-1233xf is that disclosed in WO 2012115957, which is incorporated herein by reference in its entirety.

Accordingly, in some embodiments, the process further comprises contacting 1,1,1-trifluoro-2,3-dichloropropane (HCFC-243db) with a catalyst in a reaction zone to produce a product mixture comprising 2-chloro-3,3,3-trifluoropropene (HCFO-1233xf), wherein said catalyst comprises MY supported on carbon, and M is K, Na or Cs, and Y is F, CI or Br. In some embodiments, the carbon is an activated carbon. In some embodiments, the carbon is an acid washed activated carbon. In some embodiments, M is K and Y is F or CI.

In some embodiments, the temperature in the reaction zone is from about 140° C. to about 400° C. In some embodiments, the temperature in the reaction zone is from about 150° C. to about 250° C. In some embodiments, the temperature in the reaction zone is from about 175° C. to about 225° C.

In some embodiments, the product selectivity to 2-chloro-3,3,3-trifluoropropene is at least 90 mole %. In some embodiments, the product selectivity to 2-chloro-3,3,3-trifluoropropene is at least 95 mole %. In some embodiments, the dehydrochlorination selectivity to 2-chloro-3,3,3-trifluoropropene is at least 90 mole %.

In some embodiments, the process of preparing HCFO-1233xf is that disclosed in US 20120215035, which is incorporated herein by reference in its entirety.

Accordingly, in some embodiments, the process further comprises 1,1,1-trifluoro-2,3-dichloropropane (HCFC-243db) with a catalyst in a reaction zone to produce a product mixture comprising 2-chloro-3,3,3-trifluoropropene (HCFO-1233xf).

In some embodiments, the process further comprises contacting 1,1,1-trifluoro-2,3-dichloropropane (HCFC-243db) with a chromium oxyfluoride catalyst in a reaction zone to produce a product mixture comprising 2-chloro-3,3,3-trifluoropropene (HCFO-1233xf).

In some embodiments, the process is conducted in the presence of HF. In some embodiments, the mole ratio of HF to 2-chloro-3,3,3-trifluoropropene in the reaction zone is no more than 0.9.

In some embodiments, the temperature in the reaction zone is from about 200° C. to about 500° C. In some embodiments, the temperature in the reaction zone is from about 275° C. to about 450° C.

In some embodiments, the product selectivity to 2-chloro-3,3,3-trifluoropropene is at least 90 mole %. In some embodiments, the dehydrochlorination selectivity to 2-chloro-3,3,3-trifluoropropene is at least 95 mole %.

The present application further provides a process of preparing 2-chloro-1,1,1,2-tetrafluoropropane (HCFC-244bb), comprising hydrofluorinating 2-chloro-3,3,3,-trifluoropropene (HCFO-1233xf) with HF to form 2-chloro-1,1,1,2-tetrafluoropropane (HCFC-244bb).

In some embodiments, the process of preparing HCFC-244bb is that disclosed in US 20140275648, which is incorporated herein by reference in its entirety.

Accordingly, in some embodiments, the process further comprises contacting 2-chloro-3,3,3,-trifluoropropene (HCFO-1233xf) with HF in the presence of a fluorination catalyst in multiple reaction zones under conditions effective to produce a composition that comprises 2-chloro-1,1,1,2-tetrafluoropropane (HCFC-244bb) and less than about 2% by weight 1,1,1,2,2-pentafluoropropane (HFC-245cb).

In some embodiments, the composition produced comprises less than about 1% by weight HFC-245cb. In some embodiments, the composition produced further comprises less than about 5% by weight of unreacted HCFO-1233xf. In some embodiments, the composition produced further comprises less than about 2% by weight of unreacted HCFO-1233xf.

In some embodiments, more than about 95% of the HCFO-1233xf is converted to HCFC-244bb. In some embodiments, more than about 98% of the HCFO-1233xf is converted to HCFC-244bb.

In some embodiments, the multiple reaction zones comprise multiple reactors operated in series. In some embodiments, the multiple reactors comprise at lease first and second reactors operated in series.

In some embodiments, the fluorination catalyst is selected from the group consisting of Lewis acids, transition metal halides, transition metal oxides, Group IVb metal halides, a Group Vb metal halides, or combinations thereof. In some embodiments, the fluorination catalyst is select from the group consisting of $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof.

In some embodiments, the fluorination catalyst is the same or different in each of the multiple reaction zones.

In another embodiment, the process further comprises:
a) contacting, in a first reaction zone, feed 2-chloro-3,3,3,-trifluoropropene (HCFO-1233xf) with HF and first fluorination catalyst under conditions effective to produce a first composition comprising unreacted HCFO-1233xf, a first amount of 2-chloro-1,1,1,2-tetrafluoropropane (HCFC-244bb), and a first amount of 1,1,1,2,2-pentafluoropropane (HFC-245cb);
b) contacting, in a second reaction zone, the first composition with a second fluorination catalyst under conditions to produce a second composition, wherein the second composition comprises HCFC-244bb, and less than about 5% HCFO-1233xf by weight relative to the amount of feed 1233xf, and less than about 2% by weight HFO-245cb.

In some embodiments, the second reaction zone is comprised of one or more reactors operated in series. In some embodiments, the first and the second reaction zones each comprise CSTR reactors. In some embodiments, said first composition further comprises carryover first fluorination catalyst which is removed from the first composition prior to contacting in said second reaction zone. In some embodiments, the first and second fluorination catalysts each comprise a fluorinated $SbCl_5$ species.

The present application further provides a process of preparing 2,3,3,3-tetrafluoropropene (HFO-1234yf), comprising hydrofluorinating 2-chloro-3,3,3,-trifluoropropene (HCFO-1233xf) with HF to form 2,3,3,3-tetrafluoropropene (HFO-1234yf).

The present application also provides a process of preparing 2,3,3,3-tetrafluoropropene (HFO-1234yf), comprising dehydrochlorinating 2-chloro-1,1,1,2-tetrafluoropropane (HCFC-244bb) to form 2,3,3,3-tetrafluoropropene (HFO-1234yf).

The present application additionally provides a process of preparing 2,3,3,3-tetrafluoropropene (HFO-1234yf), comprising reacting 2-chloro-1,1,1,2-tetrafluoropropane (HCFC-244bb) with caustic to form 2,3,3,3-tetrafluoropropene (HFO-1234yf).

In some embodiments, the process of preparing HFO-1234yf is that disclosed in US 20140350309, which is incorporated herein by reference in its entirety.

Accordingly, in some embodiments, the process further comprises: (a) removing impurities from a reactor such that the reactor is substantially free of impurities; (b) providing a starting composition comprising 2-chloro-1,1,1,2-tetrafluoropropane (HCFC-244bb) in the reactor under conditions effective to produce a final composition comprising 2,3,3,3-tetrafluoropropene (HFO-1234yf).

In some embodiments, the impurities in the reactor are selected from the group consisting of metal halides, metal oxides, and carbonaceous materials. In some embodiments, the metal halides comprise halides of Ni, Cr, Fe, Mo, Nb, Cu, and Co.

In some embodiments, the step of removing impurities from the reactor comprises introducing a reducing agent into the reactor under conditions effective to convert any metal halides or metal oxides into metallic metals.

In some embodiments, the reducing agent is selected from the group consisting of $H_2$, $NH_3$, CO, $C_1$-$C_{12}$ hydrocarbons, and combinations of these.

In some embodiments, the step of removing impurities from the reactor comprises introducing an oxidizing agent into the reactor under conditions effective to burn off the carbonaceous materials in the reactor.

In some embodiments, the oxidizing agent is selected from the group consisting of $H_2O$, $CO_2$, $O_2$, air, $O_3$, $Cl_2$, $N_2O$, and combinations of these. In some embodiments, the oxidizing agent comprises oxygen.

In some embodiments, the step of removing impurities from the reactor comprises physically removing carbonaceous materials, metal oxides, and metal halides from the reactor. In some embodiments, the step of physically removing the carbonaceous materials, metal oxides, and metal halides from the reactor is selected from the group consisting of electrical polishing, mechanical polishing, hydraulic methods, and combinations of these.

In some embodiments, the selectivity to 2,3,3,3-tetrafluoropropene is at least 90% or higher.

In some embodiments, the process provided here further comprises: (a) providing a starting composition comprising 2-chloro-1,1,1,2-tetrafluoropropane (HCFC-244bb) in a reactor that is substantially free from impurities; and (b) contacting the starting composition in the reactor under conditions effective to produce a final composition comprising 2,3,3,3-tetrafluoropropene (HFO-1234yf).

In some embodiments, the selectivity to 2,3,3,3-tetrafluoropropene is at least 90% or higher.

In some embodiments, the process of preparing HFO-1234yf is that disclosed in US 20140303409, which is incorporated herein by reference in its entirety.

Accordingly, in some embodiments, the process further comprises: (i) providing a composition comprising 2-chloro-1,1,1,2-tetrafluoropropane (HCFC-244bb); (ii) reducing the level of HF within the composition such that it is substantially free of HF; and (iii) contacting said starting composition with a dehydrochlorination catalyst to produce a final composition comprising 2,3,3,3-tetrafluoropropene (HFO-1234yf).

In some embodiments, the level of HF is reduced within the composition such that HF is present in the composition in an amount less than about 500 ppm. In some embodiments, the level of HF is reduced within the composition such that HF is present in the composition in an amount less than about 50 ppm. In some embodiments, reducing the HF level of the composition comprises the distilling of the HF, passing the composition through a scrubber, or passing the composition over a solid sorbent.

In some embodiments, the solid sorbent is selected from the group consisting of alumina, calcium carbonate, sodium carbonate, and sodium aluminate.

The present application further provides a process, comprising (i) providing a starting composition comprising a 2-chloro-1,1,1,2-tetrafluoropropane (HCFC-244bb) that is substantially free of HF; and (ii) contacting said starting composition with a dehydrochlorination catalyst to produce a final composition comprising 2,3,3,3-tetrafluoropropene (HFO-1234yf).

In some embodiments, the HF is present in the composition in an amount less than about 500 ppm. In some embodiments, the HF is present in the composition in an amount less than about 50 ppm.

In some embodiments, the contacting of said starting composition with a dehydrochlorination catalyst occurs in the vapor phase. In some embodiments, the contacting of said starting composition with a dehydrochlorination catalyst occurs in the liquid phase.

In some embodiments, the catalyst is selected from the group consisting of (i) one or more metal halides, (ii) one or more halogenated metal oxides, (iii) one or more zero-valent metals/metal alloys, and (iv) a combination of two or more of these.

In some embodiments, the dehydrochlorinating occurs in the vapor phase.

In some embodiments, the intermediate products made in each step are purified before reacting in the next step so that impurities in the 1234yf made in the final step can be removed to achieve the desired purity, for example >99.5% by weight. Purification techniques known in the art such as distillation, extraction, decantation, and adsorption can be used. One skilled in the art will recognize that impurities that are advantageous to remove before the final reaction step to make 1234yf are those that have, or react to form those that have, similar boiling points to 1234yf.

In some embodiments, the processes provided herein further comprise substantially isolating the 3,3,3-trifluoroprop-1-ene (i.e., 1243zf). By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds are routine in the art.

In some embodiments, the processes provided herein further comprise substantially isolating (e.g., purifying) 3,3,3-trifluoroprop-1-ene via distillation. In some embodiments, the process comprises substantially isolating the 3,3,3-trifluoroprop-1-ene by removing one or more additional components of a reaction mixture (e.g., 253fb, 1233xf, 254fb, or any combination thereof). In some embodiments, the one or more additional components of the reaction mixture are removed via distillation.

Uses

The processes provided herein are useful for preparing 3,3,3-trifluoroprop-1-ene (HFO-1234zf), a compound which may be useful in the manufacture of silicones used as hydraulic fluids or as an intermediate for producing 2,3,3,3-tetrafluoroprop-1-ene (HFO-1234yf). HFO-1234yf is useful for a wide variety of applications, such as refrigerants, uses in high-temperature heat pumps, organic Rankine cycles, as fire extinguishing/fire suppression agents, propellants, foam blowing agents, solvents, and/or cleaning fluids.

Compositions

The present application further provides compositions comprising one or more major components (e.g., 3,3,3-trifluoroprop-1-ene, 3-chloro-1,1,1-trifluoropropane, or a mixture thereof) in combination with one or more additional compounds. In some embodiments, the compositions are prepared according to one or more of the processes described herein.

The additional compounds of the compositions described herein may provide improved solubility for active ingredients in an aerosol or polymer constituents of a foam. Additionally, for refrigerant applications, such as use in air conditioning, heat pumps, refrigeration, and power cycles (e.g., organic Rankine cycles), the additional compounds may provide improved solubility with refrigeration lubricants, such as mineral oils, alkylbenzenes, synthetic paraffins, synthetic naphthenes, poly(alpha)olefins, polyol esters (POE), polyalkylene glycols (PAG), polyvinyl ethers (PVE), or perfluoropolyethers (PFPE), or mixtures thereof. Further, the presence of the additional compounds in a sample of 3,3,3-trifluoroprop-1-ene, 3-chloro-1,1,1-trifluoropropane, or a mixture thereof, may be used to identify the process by which one or more of the major components was manufactured.

Accordingly, the present application provides a composition comprising:
i) 3-chloro-1,1,1-trifluoropropane (253fb); and
ii) one or more additional compounds selected from the group consisting of 3,3,3-trifluoroprop-1-ene (1243zf), 2-chloro-3,3,3-trifluoropropene (1233xf), 1,1,1,3-tetrafluoropropane (254fb), and 1,1,1-trifluoro-2,3-dichloropropane (243db).

In some embodiments, the composition consists essentially of:
i) 3-chloro-1,1,1-trifluoropropane (253fb); and
ii) one or more additional compounds selected from the group consisting of 3,3,3-trifluoroprop-1-ene (1243zf), 2-chloro-3,3,3-trifluoropropene (1233xf), 1,1,1,3-tetrafluoropropane (254fb), and 1,1,1-trifluoro-2,3-dichloropropane (243db).

In some embodiments, the compositions provided herein are substantially free of a catalyst (e.g., a phase transfer catalyst) described herein.

In some embodiments, the compositions provided herein further comprise a catalyst described herein. In some embodiments, the catalyst is a phase transfer catalyst described herein.

In some embodiments, the composition comprises about 25 mole percent or less 3-chloro-1,1,1-trifluoropropane (253fb), for example, about 20 mole percent or less, about 15 mole percent or less, about 10 mole percent or less, about 5 mole percent or less, about 2 mole percent or less, or about 1 mole percent or less 3-chloro-1,1,1-trifluoropropane (253fb).

In some embodiments, the composition comprises about 1 to about 25 mole percent 3-chloro-1,1,1-trifluoropropane.

In some embodiments, the composition comprises about 1 to about 5 mole percent 3-chloro-1,1,1-trifluoropropane.

In some embodiments, the composition comprises about 1 to about 2 mole percent 3-chloro-1,1,1-trifluoropropane.

In some embodiments, the composition comprises about 20 to about 25 mole percent 3-chloro-1,1,1-trifluoropropane.

In some embodiments, the composition comprises about 23 to about 25 mole percent 3-chloro-1,1,1-trifluoropropane.

In some embodiments, the composition comprises about 70 mole percent or greater 3,3,3-trifluoroprop-1-ene (1243zf), for example, about 75 mole percent or greater, about 80 mole percent or greater, about 85 mole percent or greater, about 90 mole percent or greater, about 95 mole percent or greater, about 96 mole percent or greater, about 97 mole percent or greater, about 98 mole percent or greater, about 99 mole percent or greater, about 99.5 mole percent or greater, about 99.6 mole percent or greater, about 99.7 mole percent or greater, about 99.8 mole percent or greater, or about 99.9 mole percent or greater 3,3,3-trifluoroprop-1-ene.

In some embodiments, the composition comprises about 70 to about 80 mole percent 3,3,3-trifluoroprop-1-ene.

In some embodiments, the composition comprises about 74 to about 76 mole percent 3,3,3-trifluoroprop-1-ene.

In some embodiments, the composition comprises about 95 to about 99.9 mole percent 3,3,3-trifluoroprop-1-ene.

In some embodiments, the composition comprises about 98 to about 99 mole percent 3,3,3-trifluoroprop-1-ene.

In some embodiments, the composition comprises about 25 percent or less 3-chloro-1,1,1-trifluoropropane (253fb) as measured by gas chromatography/mass spectrometry (GC-MS) (e.g., % area under the curve), for example, about 20 percent or less, about 15 percent or less, about 10 percent or less, about 5 percent or less, about 2 percent or less, or about 1 percent or less 3-chloro-1,1,1-trifluoropropane (253fb) as measured by GC-MS.

In some embodiments, the composition comprises about 1 to about 25 percent 3-chloro-1,1,1-trifluoropropane as measured by GC-MS.

In some embodiments, the composition comprises about 1 to about 5 percent 3-chloro-1,1,1-trifluoropropane as measured by GC-MS.

In some embodiments, the composition comprises about 1 to about 2 percent 3-chloro-1,1,1-trifluoropropane as measured by GC-MS.

In some embodiments, the composition comprises about 20 to about 25 percent 3-chloro-1,1,1-trifluoropropane as measured by GC-MS.

In some embodiments, the composition comprises about 23 to about 25 percent 3-chloro-1,1,1-trifluoropropane as measured by GC-MS.

In some embodiments, the composition comprises about 70 percent or greater 3,3,3-trifluoroprop-1-ene (1243zf) as measured by GC-MS, for example, about 75 percent or greater, about 80 percent or greater, about 85 percent or greater, about 90 percent or greater, about 95 percent or greater, about 96 percent or greater, about 97 percent or greater, about 98 percent or greater, about 99 percent or greater, about 99.5 percent or greater, about 99.6 percent or greater, about 99.7 percent or greater, about 99.8 percent or greater, or about 99.9 percent or greater 3,3,3-trifluoroprop-1-ene as measured by GC-MS.

In some embodiments, the composition comprises about 70 to about 80 percent 3,3,3-trifluoroprop-1-ene as measured by GC-MS.

In some embodiments, the composition comprises about 74 to about 76 percent 3,3,3-trifluoroprop-1-ene as measured by GC-MS.

In some embodiments, the composition comprises about 95 to about 99.9 percent 3,3,3-trifluoroprop-1-ene as measured by GC-MS.

In some embodiments, the composition comprises about 98 to about 99 percent 3,3,3-trifluoroprop-1-ene as measured by GC-MS.

In some embodiments, the composition comprises about 0.5 mole percent or less 2-) chloro-3,3,3-trifluoropropene (1233xf), for example, about 0.4 mole percent or less, about 0.3 mole percent or less, about 0.2 mole percent or less, or about 0.1 mole percent or less 2-chloro-3,3,3-trifluoropropene.

In some embodiments, the composition comprises about 0.01 to about 0.15 mole percent 2-chloro-3,3,3-trifluoropropene.

In some embodiments, the composition comprises about 0.05 to about 0.15 mole percent 2-chloro-3,3,3-trifluoropropene.

In some embodiments, the composition comprises about 0.05 to about 0.2 mole percent 2-chloro-3,3,3-trifluoropropene.

In some embodiments, the composition comprises about 0.05 to about 0.1 mole percent 2-chloro-3,3,3-trifluoropropene.

In some embodiments, the composition comprises about 0.05 to about 0.07 mole percent 2-chloro-3,3,3-trifluoropropene.

In some embodiments, the composition comprises about 0.1 to about 0.2 mole percent 2-chloro-3,3,3-trifluoropropene.

In some embodiments, the composition comprises about 0.14 to about 0.16 mole percent 2-chloro-3,3,3-trifluoropropene.

In some embodiments, the composition comprises about 0.1 mole percent or less 1,1,1,3-tetrafluoropropane (254fb), for example, 0.075 mole percent or less, 0.05 mole percent or less, 0.025 mole percent or less, or 0.01 mole percent or less 1,1,1,3-tetrafluoropropane.

In some embodiments, the composition comprises about 0.01 to about 0.1 mole percent 1,1,1,3-tetrafluoropropane.

In some embodiments, the composition comprises about 0.01 to about 0.05 mole percent 1,1,1,3-tetrafluoropropane.

In some embodiments, the composition comprises about 0.01 to about 0.02 mole percent 1,1,1,3-tetrafluoropropane.

In some embodiments, the composition comprises about 0.5 percent or less 2-chloro-3,3,3-trifluoropropene (1233xf) as measured by GC-MS, for example, about 0.4 percent or less, about 0.3 percent or less, about 0.2 percent or less, or about 0.1 percent or less 2-chloro-3,3,3-trifluoropropene as measured by GC-MS.

In some embodiments, the composition comprises about 0.01 to about 0.15 percent 2-chloro-3,3,3-trifluoropropene as measured by GC-MS.

In some embodiments, the composition comprises about 0.05 to about 0.15 percent 2-chloro-3,3,3-trifluoropropene as measured by GC-MS.

In some embodiments, the composition comprises about 0.05 to about 0.2 percent 2-chloro-3,3,3-trifluoropropene as measured by GC-MS.

In some embodiments, the composition comprises about 0.05 to about 0.1 percent 2-chloro-3,3,3-trifluoropropene as measured by GC-MS.

In some embodiments, the composition comprises about 0.05 to about 0.07 percent 2-chloro-3,3,3-trifluoropropene as measured by GC-MS.

In some embodiments, the composition comprises about 0.1 to about 0.2 percent 2-chloro-3,3,3-trifluoropropene as measured by GC-MS.

In some embodiments, the composition comprises about 0.14 to about 0.16 percent 2-chloro-3,3,3-trifluoropropene as measured by GC-MS.

In some embodiments, the composition comprises about 0.1 percent or less 1,1,1,3-tetrafluoropropane (254fb) as measured by GC-MS, for example, 0.075 percent or less, 0.05 percent or less, 0.025 percent or less, or 0.01 percent or less 1,1,1,3-tetrafluoropropane as measured by GC-MS.

In some embodiments, the composition comprises about 0.01 to about 0.1 percent 1,1,1,3-tetrafluoropropane as measured by GC-MS.

In some embodiments, the composition comprises about 0.01 to about 0.05 percent 1,1,1,3-tetrafluoropropane as measured by GC-MS.

In some embodiments, the composition comprises about 0.01 to about 0.02 percent 1,1,1,3-tetrafluoropropane as measured by GC-MS.

In some embodiments, the composition comprises 3-chloro-1,1,1-trifluoropropane (253fb), 3,3,3-trifluoroprop-1-ene (1243zf), 1,1,1-trifluoro-2,3-dichloropropane (243db), 2-chloro-3,3,3-trifluoropropene (1233xf).

In some embodiments, the composition comprises 3-chloro-1,1,1-trifluoropropane (253fb), 3,3,3-trifluoroprop-1-ene (1243zf), 1,1,1,3-tetrafluoropropane (254fb), and 2-chloro-3,3,3-trifluoropropene (1233xf).

In some embodiments, the composition comprises 3-chloro-1,1,1-trifluoropropane (253fb), 3,3,3-trifluoroprop-1-ene (1243zf), and 2-chloro-3,3,3-trifluoropropene (1233xf).

In some embodiments, the composition comprises 3-chloro-1,1,1-trifluoropropane (253fb) and 1,1,1-trifluoro-2,3-dichloropropane (243db).

In some embodiments, the composition comprises 3-chloro-1,1,1-trifluoropropane (253fb), 1,1,1-trifluoro-2,3-dichloropropane (243db), and a catalyst. In some embodiments, the catalyst is a phase transfer catalyst described herein.

In some embodiments, the composition comprises:
  about 70 to about 80 mole percent 3,3,3-trifluoroprop-1-ene;
  about 20 to about 25 mole percent 3-chloro-1,1,1-trifluoropropane;
  about 0.05 to about 0.1 mole percent 2-chloro-3,3,3-trifluoropropene; and
  about 0.01 to about 0.05 mole percent 1,1,1,3-tetrafluoropropane.

In some embodiments, the composition comprises:
  about 74 to about 76 mole percent 3,3,3-trifluoroprop-1-ene;
  about 23 to about 25 mole percent 3-chloro-1,1,1-trifluoropropane;
  about 0.05 to about 0.07 mole percent 2-chloro-3,3,3-trifluoropropene; and
  about 0.01 to 0.02 mole percent 1,1,1,3-tetrafluoropropane.

In some embodiments, the composition comprises:
  about 95 to about 99 mole percent 3,3,3-trifluoroprop-1-ene;
  about 1 to about 2 mole percent 3-chloro-1,1,1-trifluoropropane; and
  about 0.1 to about 0.2 mole percent 2-chloro-3,3,3-trifluoropropene.

In some embodiments, the composition comprises:
  about 98 to about 99 mole percent 3,3,3-trifluoroprop-1-ene;
  about 1 to about 2 mole percent 3-chloro-1,1,1-trifluoropropane; and
  about 0.1 to about 0.2 mole percent 2-chloro-3,3,3-trifluoropropene.

In some embodiments, the composition comprises:
  about 70 to about 80 percent 3,3,3-trifluoroprop-1-ene;
  about 20 to about 25 percent 3-chloro-1,1,1-trifluoropropane;
  about 0.05 to about 0.1 percent 2-chloro-3,3,3-trifluoropropene; and
  about 0.01 to about 0.05 mole percent 1,1,1,3-tetrafluoropropane as measured by GC-MS.

In some embodiments, the composition comprises:
  about 74 to about 76 percent 3,3,3-trifluoroprop-1-ene;
  about 23 to about 25 percent 3-chloro-1,1,1-trifluoropropane;
  about 0.05 to about 0.07 percent 2-chloro-3,3,3-trifluoropropene; and
  about 0.01 to 0.02 percent 1,1,1,3-tetrafluoropropane as measured by GC-MS.

In some embodiments, the composition comprises:
  about 95 to about 99 percent 3,3,3-trifluoroprop-1-ene;
  about 1 to about 2 percent 3-chloro-1,1,1-trifluoropropane; and
  about 0.1 to about 0.2 percent 2-chloro-3,3,3-trifluoropropene as measured by GC-MS.

In some embodiments, the composition comprises:
  about 98 to about 99 percent 3,3,3-trifluoroprop-1-ene;
  about 1 to about 2 percent 3-chloro-1,1,1-trifluoropropane; and
  about 0.1 to about 0.2 percent 2-chloro-3,3,3-trifluoropropene as measured by GC-MS.

EXAMPLES

The invention will be described in greater detail by way of specific examples. The following examples are offered for illustrative purposes, and are not intended to limit the invention in any manner.

Example 1. 253fb Dehydrochlorination by NaOH without Phase Transfer Catalyst in a 400 mL Stirred Autoclave Reactor at 60° C. with 1000 RPM Agitation Rate A 12 wt % NaOH solution in water (195 g) and 3-chloro-1,1,1-trifluoropropane (i.e., 253fb; 10 g) were charged into a 400 mL autoclave and heated to 60° C. The reaction mixture was agitated at 1000 RPM (estimated to be the equivalent of 10.1 HP per 1000 gallons) at 60° C. The pressure increased continuously from 7 psig to 78 psig in about 2.5 hours which indicated the progress of reaction. After pressure of reactor stabilized, the reaction mixture was stirred for another 1.5 hours. The product was analyzed by GC/MS as shown in Table 1, and analysis showed ~98.5% of 253fb was converted to 3,3,3-trifluoroprop-1-ene (i.e., 1243zf) without use of a phase transfer catalyst.

TABLE 1

| Compounds | GC area (%) |
|---|---|
| 1243zf | 98.4515 |
| 253fb | 1.3459 |
| 1233xf | 0.1542 |
| other | 0.0484 |

Example 2. 253fb Dehydrochlorination by NaOH without Phase Transfer Catalyst in a 400 mL Stirred Autoclave Reactor at 40° C. with 1000 RPM Agitation Rate A 12 wt % NaOH solution in water (195 g) and 253fb (10 g) were charged into a 400 mL autoclave and heated to 60° C. The reaction mixture was agitated at 1000 rpm (10.1 HP per 1000 gallons) at 40° C. The pressure increased continuously from 9 psig to 27 psig in about 3.5 hours which indicated the progress of reaction. The product was analyzed by GC/MS as shown in Table 2, and analysis showed ~75.4% of 253fb was converted to 1243zf without use of a phase transfer catalyst.

TABLE 2

| Compounds | GC area (%) |
|---|---|
| 1243zf | 75.4423 |
| 253fb | 24.4328 |
| 1233xf | 0.0652 |
| 254th | 0.0127 |
| other | 0.0484 |

OTHER EMBODIMENTS

1. In some embodiments, the present application provides a process of preparing 3,3,3-trifluoroprop-1-ene, comprising reacting 3-chloro-1,1,1-trifluoropropane with a base in an aqueous solvent component, wherein the reacting is conducted in the absence of a phase transfer catalyst, wherein the aqueous solvent component comprises 0 to 40% w/w of an organic solvent.

2. The process of embodiment 1, wherein the aqueous solvent component does not comprise an organic solvent.

3. The process of embodiment 1 or 2, wherein the base is an aqueous base.

4. The process of embodiment 3, wherein the base is a metal hydroxide base, a metal carbonate base, a metal phosphate base, or a metal fluoride base.

5. The process of embodiment 3, wherein the base is NaOH, KOH, LiOH, CsOH, Ca(OH)$_2$, Zn(OH)$_2$, Na$_2$CO$_3$, K$_2$CO$_3$, K$_3$PO$_4$, Na$_3$PO$_4$, KF, or CsF.

6. The process of embodiment 3, wherein the base is KOH or NaOH.

7. The process of embodiment 3, wherein the base is NaOH.

8. The process of any one of embodiments 1-7, wherein about 0.01 to about 5 molar equivalents of base is used based on one molar equivalent of 3-chloro-1,1,1-trifluoropropane.

9. The process of any one of embodiments 1-8, wherein the reacting is conducted at a temperature of from about 20° C. to about 100° C.

10. The process of any one of embodiments 1-8, wherein the reacting is conducted at a temperature of from about 35° C. to about 80° C.

11. The process of any one of embodiments 1-10, wherein the reacting is conducted at a pressure of about −10 psig to about 500 psig.

12. The process of any one of embodiments 1-10, wherein the reacting is conducted at a pressure of about 5 psig to about 230 psig.

13. The process of any one of embodiments 1-10, wherein the reacting is conducted at a pressure of about 5 psig to about 150 psig.

14. The process of any one of embodiments 1-13, wherein the reacting comprises mixing the 3-chloro-1,1,1-trifluoropropane and base with a mixing power of from about 0.1 to about 50 horsepower per 1000 gallons of the reaction mixture.

15. The process of any one of embodiments 1-13, wherein the reacting comprises mixing the 3-chloro-1,1,1-trifluoropropane and base with a mixing power ranging from about 0.5 horsepower to about 40 horsepower per 1000 gallons of the reaction mixture.

16. The process of any one of embodiments 1-8, wherein the reacting is conducted at a temperature of from about 35° C. to about 80° C. and at a pressure of about 5 psig to about 230 psig.

17. The process of any one of embodiments 1-8, wherein the reacting is conducted at a temperature of from about 35° C. to about 80° C. and at a pressure of about 5 psig to about 150 psig.

18. The process of any one of embodiments 1-18, wherein the reaction further comprises an amine.

19. The process of any one of embodiments 1-18, wherein the 3-chloro-1,1,1-trifluoropropane is prepared by a process comprising reacting 1,1,1,3-tetrachloropropane with hydrofluoric acid.

20. The process of any one of embodiments 1-19, further comprising chlorinating 3,3,3-trifluoropropene to form 1,1,1-trifluoro-2,3-dichloropropane (HCFC-243db).

21. The process of embodiment 20, wherein said chlorinating comprises reacting with chlorine or HCl/oxygen.

22. The process of any one of embodiments 20-21, comprising dehydrochlorinating 1,1,1-trifluoro-2,3-dichloropropane (HCFC-243db) to form 2-chloro-3,3,3-trifluoropropene (HCFO-1233xf).

23. The process of embodiments 22, comprising reacting the 1,1,1-trifluoro-2,3-dichloropropane (HCFC-243db) with caustic to form 2-chloro-3,3,3-trifluoropropene (HCFO-1233xf).

24. The process of any one of embodiments 22-23, further comprising hydrofluorinating 2-chloro-3,3,3,-trifluoropropene (HCFO-1233xf) with HF to form 2-chloro-1,1,1,2-tetrafluoropropane (HCFC-244bb).

25. The process of any one of embodiments 22-23, further comprising hydrofluorinating 2-chloro-3,3,3,-trifluoropropene (HCFO-1233xf) with HF to form 2,3,3,3-tetrafluoropropene (HFO-1234yf).

26. The process of embodiment 24, further comprising dehydrochlorinating 2-chloro-1,1,1,2-tetrafluoropropane (HCFC-244bb) to form 2,3,3,3-tetrafluoropropene (HFO-1234yf).

27. The process of embodiments 24, further comprising reacting 2-chloro-1,1,1,2-tetrafluoropropane (HCFC-244bb) with caustic to form 2,3,3,3-tetrafluoropropene (HFO-1234yf).

28. A process of preparing 3,3,3-trifluoroprop-1-ene comprising reacting 3-chloro-1,1,1-trifluoropropane with aqueous NaOH, wherein the reacting is performed at a temperature of from about 35° C. to about 80° C. and at a pressure of from about 5 psig to about 230 psig, and wherein the reacting is conducted in the absence of a phase transfer catalyst and an organic solvent component.

29. The process of embodiments 28, wherein the reacting is conducted at a pressure of from about 5 psig to about 150 psig.

30. The process of embodiments 28 or 29, wherein the 3-chloro-1,1,1-trifluoropropane is prepared by reacting 1,1,1,3-tetrachloropropane with hydrofluoric acid.

31. A process of preparing a mixture of 3,3,3-trifluoroprop-1-ene (HFO-1243zf) and 2-chloro-3,3,3-trifluoropropene (HCFO-1233xf), comprising reacting a mixture of 3-chloro-1,1,1-trifluoropropane (HCFC-253fb) and 1,1,1-trifluoro-2,3-dichloropropane (HCFC-243db) with a base in an aqueous solvent component, wherein the reacting is conducted in the absence of a phase transfer catalyst, wherein the aqueous solvent component comprises 0 to 40% of an organic solvent.

32. The process of embodiment 31, wherein the aqueous solvent component does not comprise an organic solvent.

33. A composition comprising:
i) 3-chloro-1,1,1-trifluoropropane (253fb); and
ii) one or more additional compounds selected from the group consisting of 3,3,3-trifluoroprop-1-ene (1243zf), 2-chloro-3,3,3-trifluoropropene (1233xf), 1,1,1,3-tetrafluoropropane (254fb), and 1,1,1-trifluoro-2,3-dichloropropane (243db).

34. The composition of embodiment 33, wherein the composition comprises 3-chloro-1,1,1-trifluoropropane (253fb), 3,3,3-trifluoroprop-1-ene (1243zf), and 2-chloro-3,3,3-trifluoropropene (1233xf).

35. The composition of embodiment 33 or 34, wherein the composition comprises:
about 95 to about 99 percent 3,3,3-trifluoroprop-1-ene (1243zf);
about 1 to about 2 percent 3-chloro-1,1,1-trifluoropropane (253fb); and
about 0.1 to about 0.2 percent 2-chloro-3,3,3-trifluoropropene (1233xf), as measured by GC-MS.

36. The composition of embodiment 33 or 34, wherein the composition comprises:
about 98 to about 99 percent 3,3,3-trifluoroprop-1-ene (1243zf);
about 1 to about 2 percent 3-chloro-1,1,1-trifluoropropane (253fb); and
about 0.1 to about 0.2 percent 2-chloro-3,3,3-trifluoropropene (1233xf), as measured by GC-MS.

37. The composition of embodiment 33, wherein the composition comprises 3-chloro-1,1,1-trifluoropropane (253fb), 3,3,3-trifluoroprop-1-ene (1243zf), 1,1,1,3-tetrafluoropropane (254fb), and 2-chloro-3,3,3-trifluoropropene (1233xf).

38. The composition of embodiments 33 or 37, wherein the composition comprises:
about 70 to about 80 percent 3,3,3-trifluoroprop-1-ene (1243zf);
about 20 to about 25 percent 3-chloro-1,1,1-trifluoropropane (253fb);
about 0.05 to about 0.1 percent 2-chloro-3,3,3-trifluoropropene (1233xf); and
about 0.01 to about 0.05 percent 1,1,1,3-tetrafluoropropane (254fb), as measured by GC-MS.

39. The composition of embodiments 33 or 37, wherein the composition comprises:
about 74 to about 76 mole percent 3,3,3-trifluoroprop-1-ene (1243zf);
about 23 to about 25 mole percent 3-chloro-1,1,1-trifluoropropane (253fb);
about 0.05 to about 0.07 mole percent 2-chloro-3,3,3-trifluoropropene (1233xf); and
about 0.01 to 0.02 mole percent 1,1,1,3-tetrafluoropropane (254fb), as measured by GC-MS.

40. The composition of embodiment 33, wherein the composition comprises 3-chloro-1,1,1-trifluoropropane (253fb), 3,3,3-trifluoroprop-1-ene (1243zf), 1,1,1-trifluoro-2,3-dichloropropane (243db), and 2-chloro-3,3,3-trifluoropropene (1233xf).

41. The composition of embodiment 33, wherein the composition comprises 3-chloro-1,1,1-trifluoropropane (253fb), 1,1,1-trifluoro-2,3-dichloropropane (243db).

42. The composition of any one of embodiments 33 to 41, wherein the composition further comprises a catalyst.

43. The composition of any one of embodiments 33 to 41, wherein the composition is substantially free of a catalyst.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A composition comprising:
i) between about 0.1 to about 0.1 mol % 1,1,1,3-tetrafluoropropane (254fb); and
ii) about 70% or greater 3,3,3-trifluoroprop-1-ene (1243zf).

2. The composition of claim 1, wherein the composition further comprises 2-chloro-3,3,3-trifluoropropene (1233xf).

3. The composition of claim 1, wherein the composition further comprises 3-chloro-1,1,1-trifluoropropane (253fb).

4. The composition of claim 1, wherein the composition comprises 1,1,1-trifluoro-2,3-dichloropropane (243db).

5. The composition of claim 1, wherein the composition further comprises a catalyst.

6. The composition of claim 4 further comprising 1233xf.

7. The composition of claim 6 further comprising 244bb.

8. A composition comprising:
i) from about 0.01 to about 0.1 mol % 1,1,1,3-tetrafluoropropane (254fb);
ii) 3,3,3-trifluoroprop-1-ene (1243zf); and
iii) at least one member selected from the group consisting of 243db, 1233xf and 244bb.

* * * * *

UNITED STATES PATENT AND TRADEMARK OFFICE
CERTIFICATE OF CORRECTION

PATENT NO. : 11,447,438 B2
APPLICATION NO. : 17/246783
DATED : September 20, 2022
INVENTOR(S) : Xuehui Sun and Karl Robert Krause It is certified that error appears in the above-identified patent and that said Letters Patent is hereby corrected as shown below:

On the Title Page

Item (56) Right Column, "Other Publications" 7 Lines down, cancel "Hazfldine" and insert -- Haszeldine --.

In the Specification

Column 10, Line 1, cancel "(i.e., 253lb) -" and insert -- (i.e., 253fb) --.

Column 23, Table 2, Line 41, cancel "254th" and insert -- 254fb --.

In the Claims

Column 26, Claim 1, Line 46, cancel "between about 0.1 to about 0.1" and insert -- between about 0.01 to about 0.1 --.

Signed and Sealed this
Thirtieth Day of January, 2024

Katherine Kelly Vidal
*Director of the United States Patent and Trademark Office*